United States Patent [19]

Sorge et al.

[11] Patent Number: 5,112,459
[45] Date of Patent: May 12, 1992

[54] APPARATUS AND METHOD FOR TRANSFER OF MACROMOLECULES

[75] Inventors: Joseph A. Sorge, San Diego; Keith V. Sylvester, La Jolla, both of Calif.

[73] Assignee: Stratagene Cloning Systems, La Jolla, Calif.

[21] Appl. No.: 376,419

[22] Filed: Jul. 7, 1989

[51] Int. Cl.⁵ .................. G01N 27/26; B01D 57/02
[52] U.S. Cl. .................. 204/180.1; 204/299 R; 204/182.8
[58] Field of Search ............ 204/299 R, 182.8, 180.1

[56] References Cited

U.S. PATENT DOCUMENTS

| 4,726,889 | 2/1988 | Love et al. ............ 204/299 R X |
| 4,840,714 | 6/1989 | Littlehales ............ 204/180.1 |

FOREIGN PATENT DOCUMENTS

| 0293658 | 7/1988 | European Pat. Off. |
| 250337 | 4/1986 | Fed. Rep. of Germany |
| WO87/02132 | 4/1987 | PCT Int'l Appl. |

OTHER PUBLICATIONS

M. H. Johnson et al., "Identification of Protein Bands in Polyacrylamide Gel by Protein Printing" Biochimica et Biophysica Acta, 718 (1982) pp. 121-124.
M. Peferoen et al., "Vacuum-blotting: a new simple and efficient transfer of proteins from sodium dodecyl sulfate-polyacrylamide gels to nitrocellulose" FEBS Letters, vol. 145, No. 2 (Aug. 1982) pp. 369-371.
Cohen, J. H. M., Lambrey, Y., Dropsy, G. E. Instantaneous Roll-Bolt From Cellulose Acetate After Electrophoresis Aversatile Tool for Monoclonal Antibody Characterization, J. Immunological Methods 104, 25-30 (1987).
Koch, C., Skodt, K., Laursen, I. A Simple Immunoloblotting Method After Separation of Proteins in Agarose Gel, J. Immunological Methods, 84, 271-278 (1985).
Desvauz, F. X., David, B., Peltre, G. Multiple Successive Immunoprinting: A Fast Blotting Technique of a Single Agarose Isoelectric Focusing Gel Chem. Abstracts, 112, 394 (May 7, 1990).

Primary Examiner—John Niebling
Assistant Examiner—John S. Starsiak, Jr.
Attorney, Agent, or Firm—Lyon & Lyon

[57] ABSTRACT

An apparatus and method for the transfer of macromolecules from a source medium to a transfer medium employ positive pressure to urge a sample from the source medium to the transfer medium. The source and transfer media are disposed in adjacent relation, a positive pressure such as air pressure, fluid pressure, air and fluid pressure or mechanical pressure is applied against the source medium, and the molecule is recovered from the transfer medium.

40 Claims, 3 Drawing Sheets

APPARATUS AND METHOD FOR TRANSFER OF MACROMOLECULES

BACKGROUND OF THE INVENTION

The field of the present invention relates to apparatus and methods for the transfer of macromolecules such as DNA, RNA, proteins and the like from a source medium to a transfer medium, for example, following gel electrophoresis.

The transfer of DNA, RNA or proteins following gel electrophoresis is commonly carried out by three methods. The classical technique is capillary blotting which typically involves placing a piece of transfer membrane in contact with a gel and then placing absorbent paper on the other side of the transfer membrane. The molecules are removed from the gel and transferred to the transfer membrane. Typically in this procedure, the gel is continually re-hydrated by exposing the opposite side of the gel to a thoroughly soaked wick that is in contact with a large reservoir of transfer buffer.

Another method for transferring macromolecules to a transfer membrane involves the application of an electric field across the gel to electrophorese the macromolecules from the gel to the transfer membrane. This method was the first alternative to capillary blotting. It is mainly popular for the transfer of proteins to transfer membranes. However, its popularity was short lived for the transfer of DNA and RNA because of the introduction of a third type of blotting, vacuum blotting.

Vacuum blotting involves the application of a vacuum to one side of the transfer membrane such that fluid is drawn through the transfer membrane from the gel. In this system, the gel is placed in contact with a large buffer chamber directly or with a thoroughly soaked paper wick that is in contact with a large transfer buffer chamber. By application of the vacuum, fluid is drawn out of the gel and through the transfer membrane. This partially dehydrates the gel and the gel must be continually rehydrated by the flow of fluid from the buffer chamber. This flow is typically governed by simple gravitational and capillary forces. U.S. Pat. No. 4,726,889 discloses one such vacuum blotting system.

Of the three methods, vacuum blotting tends to be the most rapid. However, both vacuum blotting and electroblotting have disadvantages, as described below, which tend to limit the effectiveness of those methods, particularly where the macromolecule of interest is DNA or RNA. For that reason, classical capillary blotting is still the most popular method employed for the transfer of DNA and RNA. For protein blotting, however, electroblotting is used almost exclusively.

A disadvantage of electroblotting for DNA and RNA is that the resolution of the DNA fragments on the transfer membrane is not as effective as with capillary blotting nor is the efficiency of the transfer. The disadvantages of vacuum blotting are twofold. First, the technique is somewhat cumbersome and most vacuum blotting apparatus tend to develop leaks of either fluid or air that frequently cause the transfer to be either uniformly inefficient or inefficient in local regions of the transfer membrane. A second disadvantage to vacuum blotting is that only a minimum amount of vacuum can be applied against the transfer membrane and one side of the gel, otherwise the gel will collapse. This is typically a vacuum of about 30-35 mm Hg below atmospheric pressure (all references made hereinafter to pressure are with respect to atmospheric pressure). If a vacuum exceeding about 30-35 mm of mercury is used, fluid is drawn from the gel too rapidly and rehydration of the gel is not quick enough to prevent the gel matrix from collapsing. Collapse of the gel can be recognized by a decrease in the thickness of the gel and results in the cessation of transfer of large molecules from the gel to the membrane. Therefore, once a gel has collapsed the efficiency of the overall transfer is decreased, sometimes substantially. This limitation on the amount of vacuum that can be applied limits both the speed and/or the overall efficiency of the transfer process. Because of the limitations inherent in vacuum blotting, those who work with DNA and RNA have elected to remain with capillary blotting, even though capillary blotting commonly requires six to twelve hours compared to vacuum blotting which requires one to two hours.

In view of the lengthy time periods involved in capillary blotting, the unreliable nature and relative inefficiency of vacuum blotting, and the inaccurate and relatively unfocused transfer of macromolecules using the electrotransfer method, there exists a need for an alternative means to accomplish the transfer of macromolecules to a transfer medium. The present invention meets this need by providing an improved method and apparatus for the transfer of molecular components in an efficient, reliable, and accurate manner.

SUMMARY OF THE INVENTION

The present invention is directed to an apparatus and method wherein positive pressure is employed in order to facilitate molecular transfer without the deficiencies of the blotting methods of the prior art. To that end, one side of a source medium such as a gel may be exposed to a positive pressure. The low pressure side of the medium is exposed to a transfer medium such as a transfer membrane. Application of a positive pressure against the pressure side of the source medium displaces the molecules from the source medium to the transfer medium. In accordance with the invention, this may be accomplished by a variety of means including, for example, means for applying air pressure, fluid pressure, air and fluid pressure, or means for squeezing the source medium. Preferably, however, the introduction of a positive pressure is accomplished by means for applying air and fluid pressure in combination.

DETAILED DESCRIPTION OF PREFERRED EMBODIMENTS

Figure 1:
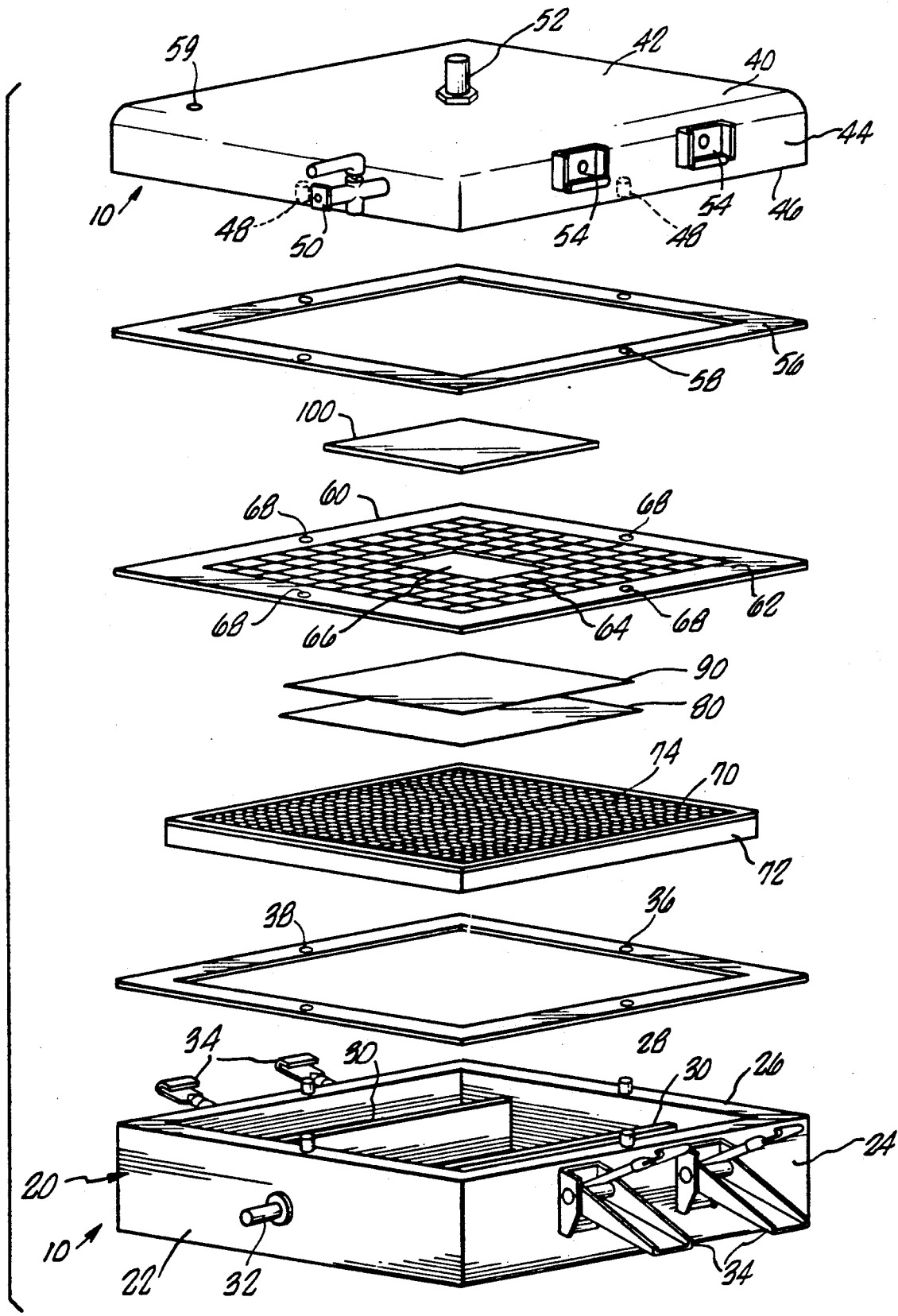
FIG. 1 is an exploded perspective view of an apparatus constructed in accordance with the present invention.

Having reference to FIG. 1, the present invention may be embodied as an enclosure generally designated as 10 comprising a base 20 and lid 40. The enclosure 10 may be constructed of durable acrylic or any other material suitable as a pressure bearing material. Acrylic, however, is durable, attractive and readily washable. The base 20 is generally rectangular in shape and includes a substantially planar bottom member 22 and sides 24 extending to a continuous substantially planar sill 26. Extending from the sill 26, perpendicularly to the plane of the bottom member 22, are four guides 28 which are shown in the Figure as being generally cylindrical in shape.

Mounted to the bottom member 22 and the sides 24 are a pair of grid support members 30. The grid support members are substantially rectangular in shape, although many other support configurations, such as a lip formed on the sides 24, would also be possible. Extending through one of the sides 24 is a pressure fitting 32 providing a vent or pressure exhaust port. Attached to opposing sides 24 of the base 20 are four draw latches 34 formed of stainless steel or like material, which are adjustable to assure a tight pressure seal. Mounted on the sill 26 is a sealing gasket 36. The seal 36 is provided with apertures 38 which are adapted to align with and receive the guides 28.

The lid 40 is generally rectangular in shape and includes a top portion 42 and four sides 44 extending therefrom to a continuous substantially planar sill 46. The sill 46 is provided with four recesses 48 which are adapted to align with and receive the guides 28 of the base 20. Mounted to one of the sides 44 of the lid 40 is a petcock fitting 50 providing a fluid outlet for the removal of a buffer solution Mounted to the top portion 42 of the lid 40 is a pressure fitting 52 providing a pressure inlet and fluid introduction port. Four stainless steel catches 54 are mounted to opposing sides 44 and are positioned to engage the latches 34 on the base 20. Mounted to the sill 46 is a sealing gasket 56 provided with four apertures 58 which are adapted to align with and receive the guides 28 on the base 20. Finally, a bleed valve 59 is provided in the top 42 of the lid 40 to serve as a safety pressure relief valve.

Adapted for placement between the base 20 and the lid 40 in sealing engagement therewith is a generally rectangular substantially planar pressure member or mask 60. The pressure member 60 includes a perimeter 62 and an interior 64. The pressure member 60 may be made from VERILON TM or any other suitable material which is generally impermeable to liquids and gases. Centrally disposed in the interior 64 is an opening 66 which is preferably cut so as to be smaller in area than a gel sample to be used with the apparatus. The opening may comprise a single aperture or may include two or more apertures. The opening could also comprise multiple apertures. The opening could also comprise multiple apertures as would be provided, for example, by a permeable grating or grid. The perimeter 62 of the mask 60 is substantially the same shape and size as the sills 26 and 46 and the seals 36 and 56, and includes four apertures 68 which are adapted to align with and receive the guides 28 on the base 20.

Positioned below the pressure member 60, on the grid support members 30, is a membrane support grid 70. The support grid 70 comprises a frame 72 which rests on the support members 30, and a liquid permeable interior matrix 74 which provides support for a transfer membrane In operation, the base 20 and the lid 40 are latched together with the pressure member 60 disposed between the seals 36 and 56. Thus configured, the pressure member 60 defines in combination with the top 42 and sides 44 of the lid 40 a first chamber which may be deemed a pressure chamber. The pressure chamber serves as a buffer reservoir (for pressurized air and/or buffer) for pressurizing the source medium. The pressure member 60 also defines in combination with the bottom 22 and sides 24 of the base 20 a second chamber which may be deemed a collection chamber.

To operate the apparatus of FIG. 1, the base 20 is placed on a level surface and the support grid 70 is placed on the grid support members 30. The seal 36 is usually already adhesively bonded to the sill 26 and thus need not be mounted each time the apparatus is used. A sheet of filter paper 80 and a Nylon or other suitable transfer membrane 90 are placed in overlying relation on the matrix 74 of the support grid 70, at a central location thereon, so as to ensure that the membrane will align with the central opening 66 in the pressure member 60. The pressure member 60 is then placed on the seal 36 with the guides 28 extending through the openings 68 therein. A gel 100 with a molecular sample of interest in placed on the support surface provided by the interior portion 64 of the pressure member 60, so as to cover the opening 66 therein. The lid 40, with the seal 56 usually already bonded to the sill 46, is then placed on the base 20. The system is made air tight by latching the latches 34.

Figure 2:
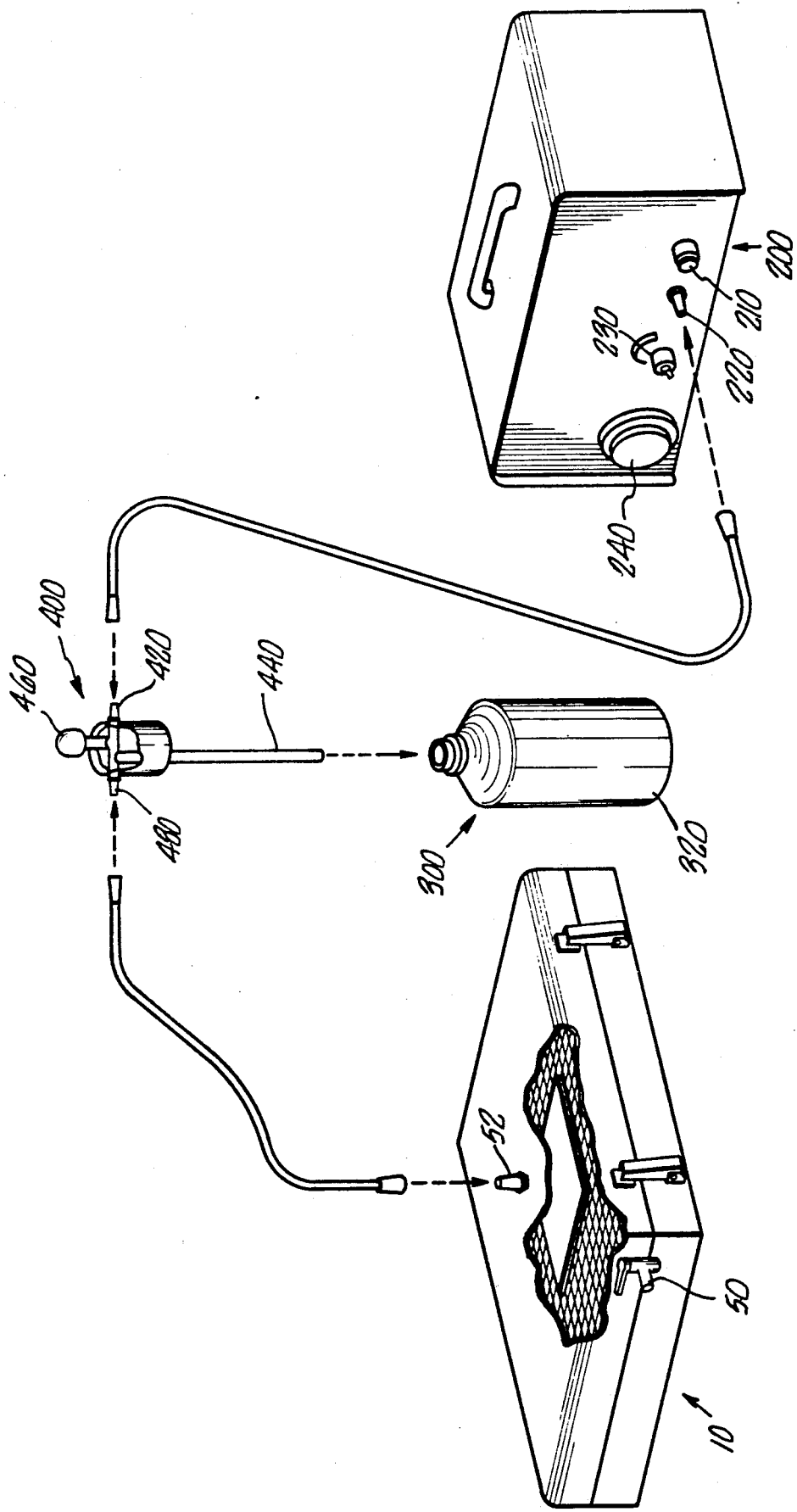
FIG. 2 is a diagrammatic representation of an apparatus constructed in accordance with the present invention including a pressure and fluid supply.

Referring to FIG. 2, the enclosure 10 is operatively connected to a pressure source 200 and a fluid source 300. The pressure source 200 may be a conventional air pressure source, typically electrically powered, capable of providing at least 30 mm, but preferably up to 200 mm Hg positive pressure. The pressure source 200 includes a power switch 210, a pressure outlet 220, a pressure adjustment 230 and a pressure gauge 240. The pressure source is connected through a first pressure feed line to a fluid source 300. The fluid source 300 includes a fluid reservoir, i.e., the bottle 310, and a control valve 400.

The control valve 400 comprises an inlet 420 to which is connected the feed line from the pressure source 200. The control valve 400 further includes a fluid intake 440 which extends into the fluid contained in the fluid source 300, and a plunger 480 which, when depressed, directs pressurized air from the source feed line into the bottle 300, thereby displacing fluid contained therein upwardly through the intake 440. Depending on the position of the plunger, either pressurized air or fluid will exit the control valve 400, through an outlet 480, to a second feed line which is operatively connected to the pressure fitting 52 on the lid 40 of the enclosure 10.

With the latches secured, and with the fluid reservoir filled with an appropriate liquid, such as a transfer buffer, the enclosure may be first pressurized with air pressure only. This ensures that the gel will be firmly seated on the pressure member 60. The operator may then depress the plunger 460, thereby directing buffer into the pressure chamber, until the buffer level is several millimeters above the gel. At that point, the plunger may be raised to its original position and additional pressurized air introduced. It has been determined that a final positive pressure of at least substantially 75 mm Hg, and preferably 100 mm Hg may be advantageously applied. The pressure is maintained for a period which may range up to 120 minutes or more depending on the investigator but which is usually about fifteen minutes for standard thickness gels. Because there is a pressure difference between the buffer in the pressure chamber and the atmospheric pressure in the collection chamber, fluid begins to flow from the buffer into the gel and then through the gel across the transfer membrane and into the collection chamber, where the transfer membrane is positioned to receive the sample. After transfer of the sample to the transfer membrane 50, the buffer is pressurized out of the system through the petcock 50 (to e.g., a drain hose), the unit is disassembled and the membrane 90 is removed.

Alternatives to the above-described pressurization means and method would also be possible. For example, the pressure chamber could be filled entirely with pressurized buffer solution. Alternatively, the pressure chamber could be pressurized with a gas, such as air, without the inclusion of a liquid or transfer buffer in the chamber. The compressed air or gas would place pressure directly on the gel. Alternatively, the pressure chamber may be sized so as to be approximately the actual size of the gel and provided with means to squeeze the gel to displace molecules from the gel to the transfer membrane.

An advantage of the foregoing apparatus and method is that substantially more pressure can be applied to the gel than with vacuum blotting. It is believed that the gel is never partially dehydrated as it is with vacuum blotting and thus there is not the same tendency for the gel to collapse. It has been determined experimentally that at least a positive pressure of 100 mm Hg can be applied and that there is substantially more rapid transfer from the gel to the membrane as compared for the same length of time with vacuum blotting at negative 30 mm Hg. At 100 mm Hg positive pressure, no evidence of gel collapse was found. Although this improvement in transfer rate has not been precisely quantified, it is believed to vary linearly with the pressure. Thus, pressure blotting at 100 mm Hg is likely to transfer macromolecules from a gel to a membrane in one third less time than vacuum blotting at negative 30 or 35 mm Hg. Alternatively, if vacuum blotting and pressure blotting are carried out for the same period of time, it is believed that three times as many molecules can be transferred with pressure blotting at 100 mm Hg as compared with vacuum blotting at negative 35 mm Hg, provided neither system has either depleted the gel of molecules or saturated the binding capacity of the transfer membrane.

Figure 3A:
FIG. 3a and 3b are a comparison of autoradiograms of radioactive DNA transferred by vacuum blotting and by blotting in accordance with the present invention.
Figure 3B:
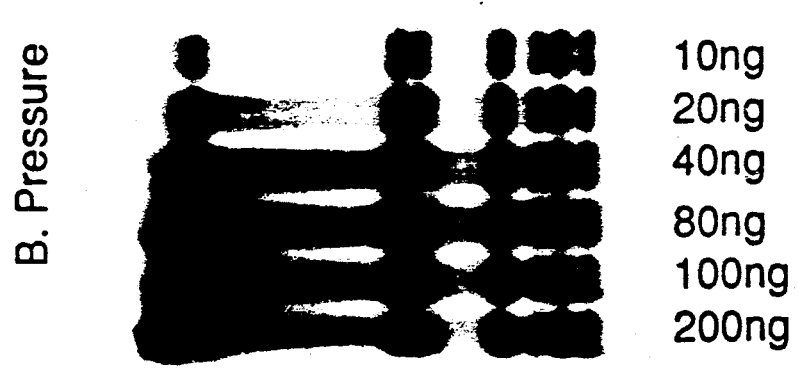

To demonstrate the advantages of the present invention over vacuum blotting, two essentially identical agarose gels containing essentially identical amounts of radioactively labeled DNA were placed in either a vacuum blotting apparatus or a pressure blotting apparatus. Each gel contained separate specimens of the same DNA at several concentrations: The radioactively labeled DNA in one gel was transferred using a standard vacuum blotting procedure at negative 35 mm of mercury. The radioactively labeled DNA samples in the other gel were transferred using the pressure blotting apparatus of the present invention at positive 100 mm of mercury. Both transfers were carried out for 15 minutes. The transfer membranes were removed and exposed to x-ray film for the same length of time. As shown in FIG. 3, the pressure blotting method of the present invention yielded a significantly more intense signal at all concentrations of the DNA samples.

Accordingly, an apparatus and method for the transfer of macromolecular samples from a source medium to a transfer medium using a positive pressure are disclosed herein. While embodiments and applications of this invention are shown and described, it will be apparent to those skilled in the art that many more modifications are possible without departing from the inventive concepts herein. For example, it is believed that both the source and transfer media can be placed on the pressure member 60 without the support grid. Moreover, it is believed that the collection side of the transfer membrane need not necessarily be at atmospheric pressure. Still further, a variety of pressure application methods can be suitably employed such as air only, fluid only, air-fluid, or by squeezing the gel. The invention therefore is not to be restricted except in the spirit of the appended claims.

What is claimed is:

1. An apparatus for transferring a molecular sample from a source medium to a transfer medium comprising means for supporting a source medium in adjacent relation with a transfer medium and means for applying a positive pressure against said source medium, wherein said pressure application means comprise gaseous or fluid pressure and the positive pressure is greater than atmospheric pressure, whereby the molecular sample may be displaced from said source medium to said transfer medium.

2. The apparatus set forth in claim 1 wherein said pressure application means comprise introducing gaseous pressure.

3. The apparatus set forth in claim 1 wherein said pressure application means comprise means for introducing fluid pressure.

4. An apparatus for transferring a molecular sample from a source medium to a transfer medium comprising means for supporting a source medium in adjacent relation with a transfer medium and means for applying a positive pressure against said source medium, whereby the molecular sample may be displaced from said source medium to said transfer medium wherein said pressure application means comprise means for introducing gaseous pressure followed by fluid pressure.

5. The apparatus set forth in claim 1 wherein said pressure application means comprise means for squeezing the source medium.

6. An apparatus for transferring molecular components from a source medium to a transfer medium comprising means for applying a positive pressure against the source medium, the positive pressure being greater than atmospheric pressure, including a pressure chamber having a transfer opening formed therein, and means for supporting the source and transfer media in adjacent relation across said transfer opening, whereby molecular components in the source medium may be displaced toward the transfer medium under action of the positive pressure.

7. The apparatus set forth in claim 6 further including a collection chamber to which said transfer opening opens, said collection chamber having a vent therein.

8. The apparatus set forth in claim 6 wherein said pressure chamber includes an inlet for introducing a buffer solution therein.

9. The apparatus set forth in claim 6 wherein said means for supporting the source and transfer media include a support grid disposed adjacent said transfer opening.

10. The apparatus set forth in claim 6 wherein said means for supporting the source and transfer media include a pressure member defining in part said pressure chamber and having formed therein said transfer opening.

11. The apparatus set forth in claim 6 wherein said means for supporting the source and transfer media include a pressure member defining in part said pressure chamber and having formed therein said transfer opening, and a support grid disposed adjacent said pressure member, said pressure member being adapted to support a source medium and said support grid being adapted to support a transfer medium.

12. The apparatus set forth in claim 6 wherein said transfer opening comprises a single opening sized to be smaller than a source medium in order to support the medium during application of a positive pressure thereon.

13. The apparatus set forth in claim 6 wherein said transfer opening comprises two openings sized to be smaller than two source media in order to support the media during application of a positive pressure thereon.

14. The apparatus set forth in claim 6 wherein said apparatus further comprises a base upon which the pressure chamber is supported, the pressure chamber being defined by a lid removably connected by latching means to the base and a pressure member.

15. An apparatus for transferring molecular components from a source medium to a transfer medium comprising means for applying a positive pressure against the source medium, including a pressure chamber having a transfer opening formed therein, and means for supporting the source and transfer media in adjacent relation across said transfer opening, whereby molecular components in the source medium may be displaced toward the transfer medium under action of the positive pressure, wherein said apparatus comprises a base and a lid removably connected at an interface, and a pressure member disposed across said interface defining in combination with said lid said pressure chamber and having formed therein said transfer opening.

16. The apparatus set forth in claim 15 wherein said pressure member comprises a perimeter portion forming said interface and a central portion disposed interiorly of said perimeter portion, said transfer opening comprising an opening disposed in said central portion of said pressure member.

17. The apparatus set forth in claim 15 wherein said apparatus comprises said base and said lid removably joined at an interface by latching means, said lid including a pressure inlet and a fluid outlet for removal of a liquid from said pressure chamber, said base including a port providing a vent to atmosphere, said pressure member comprising a perimeter portion forming said interface and a central portion disposed interiorly of said perimeter portion having said transfer opening centrally disposed therein, a collection chamber being defined by said base and said pressure member.

18. The apparatus set forth in claim 17, including a source of pressurized gas having an output connected to a valve mounted to a fluid source, said valve being connected in turn to said pressure inlet and being adjustable from a position wherein pressurized gas in provided to said pressure inlet.

19. The apparatus set forth in claim 18 further including a support grid disposed adjacent said pressure member, removably supported by support means disposed in said base.

20. The apparatus set forth in claim 19 wherein said lid comprises a top portion with side portions extending therefrom, said base comprises a bottom portion with side portions extending therefrom, which side portions extend to an interface surface, respectively, each said surface engaging said perimeter portion of said pressure member when said lid and base are joined.

21. The apparatus set forth in claim 20 further including seal members disposed at the interface surfaces of said lid and base for sealing engagement with said perimeter portion of said pressure member when said lid and said base are joined.

22. The apparatus set forth in claim 21 further including guides extending from the interface surface of said base, and recesses disposed in the interface surface of said lid adapted to receive said guides, said perimeter portion of said pressure member and said seal members disposed on said interface surfaces being appropriately apertured to receive said guides.

23. A method for transferring molecular components from a source medium to a transfer medium comprising the steps of placing a source medium in proximal relation to a transfer medium, and applying a positive pressure to said source medium, wherein said positive pressure is greater than atmospheric pressure and said pressure is provided by any combination of pressurized gas and liquid, whereby molecular components are displaced from said source to said transfer medium.

24. The method set forth in claim 23 wherein said positive pressure is provided by pressurized gas or liquid.

25. A method for transferring molecular components from a source medium to a transfer medium comprising the steps of placing a source medium in proximal relation to a transfer medium, and applying a positive pressure to said source medium, whereby molecular components are displaced from said source to said transfer medium wherein said positive pressure is applied by applying a pressurized gas, followed by a liquid.

26. The method set forth in claim 23 wherein said positive pressure is provided by pressurized gas only.

27. The method set forth in claim 23 wherein said positive pressure is provided by pressurized liquid only 28. The method set forth in claims 23, 24 or 25 wherein said positive pressure is additionally provided by mechanical means acting on the source medium.

29. The method set forth in claims 23, 24, 25, 26, or 27 wherein said molecular components are selected from DNA, RNA or proteins.

30. The method set forth in claim 23, 24, 25, 26, or 27 wherein said source medium is an agarose gel and said transfer medium is a membrane.

31. The method set forth in claims 23, 24, 25, 26, or 27 wherein said molecular components comprise DNA, RNA or proteins, said source medium is an agarose gel and said transfer medium is a membrane.

32. The method set forth in claim 31 wherein a filter is disposed adjacent to said membrane, away from said gel.

33. A method for transferring molecular components from a source medium to a transfer medium comprising the steps of placing a source medium in proximal relation to a transfer medium, and applying a positive pressure greater than atmospheric pressure to said source medium, whereby molecular components are displaced from said source to said transfer medium, wherein said pressure applied to one side of the source medium is at least substantially 75 mm Hg above the pressure exerted on the opposite side of the transfer medium.

34. A method for transferring molecular components from a source medium to a transfer medium comprising the steps of placing a source medium in proximal relation to a transfer medium, and applying a positive pressure greater than atmospheric pressure to said source medium from a source of gas pressure and/or a source of fluid, said gas pressure and fluid sources being operatively associated with each other and with said source medium, and being selectively operable to provide either gas, fluid or a combination thereof to said source medium.

35. An apparatus for transferring a macromolecule such as DNA from a source medium such as an agarose gel to a transfer medium such as a membrane, comprising a base, said base including a generally planar bottom portion and sides extending from said bottom portion to a continuous base sill, base latching means attached to said sides, a vent extending from the interior of said base to the exterior thereof, grid support members disposed interiorly in said base and guides extending from said base sill, a lid, said lid comprising a top portion and sides extending from said top portion to a continuous lid sill, top latching means attached to said sides adapted to engage said base latching means, a pressure inlet disposed in said lid for connection to an external positive pressure source, a fluid inlet for introducing a buffer solution and recesses disposed in said lid sill adapted to receive said guides, a pair of pressure seals disposed on said sills, a membrane support grid disposed on said grid support members, and a pressure member comprising a perimeter portion disposed between said seals and an interior portion having an opening therein providing a passage for pressurized air.

36. The apparatus set forth in claim 1 wherein said pressure application means comprise means for introducing gaseous and fluid pressure.

37. The method set forth in claim 28 wherein said molecular components are selected from DNA, RNA or proteins.

38. The method set forth in claim 28 wherein said source medium is an agarose gel and said transfer medium is a membrane.

39. The method set forth in claim 28 wherein said molecular components comprise DNA, RNA or proteins, said source medium is an agarose gel and said transfer medium is a membrane.

40. The method set forth in claim 39 wherein a filter is disposed adjacent to said membrane, away from said gel.

* * * * *